United States Patent [19]

Doehler

[11] Patent Number: 4,478,173

[45] Date of Patent: Oct. 23, 1984

[54] METHOD AND APPARATUS FOR SENSING AND CONTROLLING THE INTENSITY OF ENERGY IN A DEPOSITION SYSTEM

[75] Inventor: Joachim Doehler, Union Lake, Mich.

[73] Assignee: Energy Conversion Devices, Inc., Troy, Mich.

[21] Appl. No.: 486,136

[22] Filed: Apr. 18, 1983

[51] Int. Cl.$^3$ ............................................. C23C 13/08
[52] U.S. Cl. .................................. 118/688; 118/50.1; 118/708; 427/10; 427/39
[58] Field of Search ..................... 427/8, 9, 10, 38, 39, 427/40, 41; 118/663, 688, 708, 50.1; 250/374, 382, 379; 364/468, 469, 500

[56] References Cited

U.S. PATENT DOCUMENTS

| | | | |
|---|---|---|---|
| 3,441,836 | 4/1969 | Riley | 364/500 |
| 3,738,926 | 6/1973 | Westwood et al. | 118/688 |
| 4,036,167 | 7/1977 | Lu | 427/10 |
| 4,242,188 | 12/1980 | Niinomi et al. | 427/41 |
| 4,332,833 | 6/1982 | Aspnes et al. | 427/85 |
| 4,405,989 | 9/1983 | Tsukada et al. | 364/468 |

Primary Examiner—John H. Newsome
Attorney, Agent, or Firm—Marvin S. Siskind; Ronald W. Citkowski

[57] ABSTRACT

A method of and apparatus for accurately sensing and reproducibly controlling the intensity of electromagnetic energy in the decomposition region of a deposition chamber. The apparatus includes a detector adapted to (1) monitor the level of radiation emitted from the decomposition region and (2) provide an output signal indicative of said level. The invention further includes circuitry for (1) comparing the signal from the detector with a reference signal indicative of a preselected level of energy, and (2) generating a correction signal indicative of the actual level of energy in the decomposition region relative to the preselected level of energy. According to the method of this invention, the correction signal may be utilized to regulate the source of electromagnetic energy so that the preselected level of electromagnetic energy within the decomposition region is kept constant despite fluctuations in other operating parameters.

3 Claims, 4 Drawing Figures

METHOD AND APPARATUS FOR SENSING AND CONTROLLING THE INTENSITY OF ENERGY IN A DEPOSITION SYSTEM

FIELD OF THE INVENTION

This invention relates generally to apparatus for producing improved photovoltaic devices and more particularly to a method and apparatus for accurately monitoring and reproducibly controlling the intensity of energy present in the decomposition region of deposition apparatus.

BACKGROUND OF THE INVENTION

This invention relates to a method and apparatus for accurately sensing and reproducibly controlling the intensity of energy of a gaseous material activated by a source of energy. In its most preferred form, this invention is specially suited for use in the mass production of amorphous (as defined hereinafter) semiconductor devices by deposition processes in which it is helpful to determine and control the energy level to which said gaseous material is subjected.

Glow discharge deposition comprises one method of mass producing amorphous semiconductor devices. It is a process carried out at less than atmospheric pressure, wherein at least one reactant gas, introduced into a sealed deposition chamber, is decomposed under the effects of an electromagnetic field developed in a portion (the decomposition region) of that chamber. Whether the electromagnetic energy is provided by alternating current, direct current, radio frequency, or microwave frequency, it is adapted to excite the atoms and molecules of the reactant gas(es), causing the products of the gaseous decomposition to be deposited upon a substrate located within the deposition chamber. The present invention is directed toward the novel concept of accurately sensing and reproducibly controlling the intensity of the electromagnetic energy introduced into the deposition chamber for decomposing the reactant gas(es).

It is to be noted that, as used herein: (1) the term "reactant gas" defines the process gas or gases from which the material (in the preferred embodiment, semiconductor material) deposited upon the substrate is derived, whether the reactant gas(es) comprise a single species, or a mixture of species, and may include an inert carrier gas admixed therewith; (2) the term "glow discharge deposition" includes all deposition processes wherein the reactant gas(es) is decomposed by electromagnetic energy regardless of whether (a) a visible glow is developed, or (b) an additional source(s) of energy, such as thermal energy, is utilized in conjunction with the electromagnetic energy; and (3) the term "amorphous" includes all alloys or materials which have long range disorder, although they may have short or intermediate range order or even contain, at times, crystalline inclusions.

Recently, considerable efforts have been made to develop systems for depositing amorphous semiconductor materials, each of which can encompass relatively large areas and which can be doped to form p-type and n-type materials for the production of p-i-n type photovoltaic devices which are, in operation, substantially equivalent to their crystalline counterparts.

It is now possible to prepare amorphous silicon alloys by glow discharge deposition or vacuum deposition techniques. The amorphous silicon alloys so prepared posses (1) acceptable concentrations of localized states in the energy gaps thereof, and (2) high quality electronic properties. Such techniques are fully described in U.S. Pat. No. 4,226,898, entitled Amorphous Semiconductors Equivalent To Crystalline Semiconductors, issued to Stanford R. Ovshinsky and Arun Madan on Oct. 7, 1980; U.S. Application Ser. No. 423,424 of Stanford R. Ovshinsky, David D. Allred, Lee Walter, and Stephen J. Hudgens entitled Method Of Making Amorphous Semiconductor Alloys And Devices Using Microwave Energy; and U.S. Pat. No. 4,217,374, of Stanford R. Ovshinsky and Masatsugu Izu, which issued on Aug. 12, 1980, also entitled Amorphous Semiconductor Equivalent To Crystalline Semiconductors. As disclosed in these patents, fluorine introduced into the amorphous silicon semiconductor layers operates to substantially reduce the density of the localized states therein.

The concept of utilizing multiple cells, to enhance photovoltaic device efficiency, was described at least as early as 1955 by E. D. Jackson in U.S. Pat. No. 2,949,498 issued Aug. 16, 1960. The multiple cell structures therein discussed utilized p-n junction crystalline semiconductor devices. Essentially the concept employed different band gap devices to more efficiently collect various portions of the solar spectrum and to increase open circuit voltage (Voc). Further, by definition, a tandem cell device has two or more cells with the light directed serially through each cell. In the first cell a large band gap material absorbs only the short wavelength light, while in subsequent cells smaller band gap materials absorb the longer wavelengths of light which pass through the first cell. The overall open circuit voltage in a tandem cell is therefore the sum of the open circuit voltage of each cell, while the short circuit current thereof is maintained substantially constant.

Unlike crystalline silicon which is limited to batch processing for the manufacture of solar cells, amorphous silicon alloys can be deposited in multiple layers over large area substrates to form solar cells in a high volume, continuous processing system. Continuous processing systems of this kind are disclosed, for example, in pending patent applications: Ser. No. 151,301, filed May 19, 1980, for A Method Of Making P-Doped Silicon Films And Devices Made Therefrom; Ser. No. 244,386, filed Mar. 16, 1981, for Continuous Systems For Depositing Amorphous Semiconductor Material; Ser. No. 240,493, filed Mar. 16, 1981, for Continuous Amorphous Solar Cell Production System; Ser. No. 306,146, filed Sept. 28, 1981, for Multiple Chamber Deposition And Isolation System And Method; and Ser. No. 359,852, filed Mar. 19, 1982, for Method And Apparatus for Continuously Producing Tandem Amorphous Photovoltaic Cells. As disclosed in these applications, a substrate may be continuously advanced through a succession of deposition chambers, wherein each chamber is dedicated to the deposition of a specific semiconductor material. In making a solar cell of p-i-n type configurations, the first chamber is dedicated for depositing a p-type semiconductor alloy, the second chamber is dedicated for depositing an intrinsic amorphous semiconductor alloy, and the third chamber is dedicated for depositing an n-type semiconductor alloy. Since each deposited semiconductor alloy, and especially the intrinsic semiconductor alloy, must be of high purity, the deposition environment in the intrinsic deposition chamber is isolated from the doping constituents within the other chambers to prevent the back diffusion of doping constituents into the intrinsic chamber.

In addition to such factors as the isolation of the reactant gas(es) in adjacent deposition chambers of the deposition apparatus, all parameters influencing the disassociation and recombination (hereinafter referred to as "decomposition") of those gas(es) must be closely controlled in order to reproducibly manufacture high quality photovoltaic devices. Since the semiconductor layers are formed by the decomposition of the reactant gases under the influence of an electromagnetic field, it follows that the electrical, chemical and optical properties of those layers are directly related to the parameters of the decomposition process. More specifically, even small variations in the amount of electromagnetic energy delivered to the decomposition region of a decomposition chamber for disassociating and recombining the reactant gas(es), can correspondingly alter (1) the chemical composition of the semiconductor material deposited upon the substrate; (2) the rate of deposition of the semiconductor material onto the substrate; (3) the electrical and optical properties exhibited by the deposited semiconductor material; and (4) make the reproducibility of uniform semiconductor materials virtually impossible. The importance of reproducibility in the production of semiconductor devices cannot be emphasized too strongly. Since, as previously mentioned, even minor changes in the compositional properties of a semiconductor material can result in material changes in its electronic and optical properties, (such as band-gap, density of states, and photoconductivity), the electromagnetic field must be carefully controlled in order to control said compositional properties of the semiconductor material. More particularly, the (1) strength of the electromagnetic field in which the reactant gases are disassociated and recombined, and (2) length of time which the reactant gases are subjected to that electromagnetic energy determines the chemical bonding and composition of the semiconductor material deposited onto the substrate. If the strength or intensity of the electromagnetic energy delivered to the decomposition region of a deposition chamber is not kept constant from one day's production of semiconductor material to the next day's production, the electrical and optical properties of that material will vary from day-to-day. However, the problem is still more difficult. It has been determined that the electromagnetic energy introduced into the decomposition region often varies with (1) time or (2) changes in other operational parameters, thereby making it impossible to reproduce results even within the same run. It should be quite apparent that such results are intolerable, not only from a manufacturing standpoint, but from a research and development standpoint as well. In order to improve the quality of photovoltaic devices, it is essential that laboratory results be reproducible for succeeding experiments and for a reduction of those experimental achievements and results to a production mode of operation.

Accordingly, there exists a need for a method of and apparatus adapted to accurately monitor and control the intensity of electromagnetic energy employed to decompose reactant gas(es) in glow discharge deposition apparatus, thereby reproducibly controlling the composition and deposition rate of the semiconductor material deposited onto the substrate. As alluded to hereinabove, initial attempts at achieving this control merely consisted of setting the source of electromagnetic energy, such as a radio frequency generator, at a constant preselected value and assuming the level of electromagnetic energy delivered from that source to the decomposition region of the deposition apparatus would remain constant. This assumption proved incorrect and led to the development of the monitoring and control system disclosed herein.

Simply setting the source of energy to deliver a constant level of electromagnetic energy to the decomposition region of a deposition chamber fails to provide a constant level of power actually acting to decompose the reactant gas(es), since factors such as the coupling of the electromagnetic energy to those reactant gas(es), heat losses, impedance matching, temperature differentials, etc. are not taken into account. Of the aforementioned factors, it appears that the impedance tuning is the most critical. As the deposition system operates, the various components thereof may heat up or cool down, thereby disrupting the transfer of power through the system. Therefore, the amount of power delivered by the source of electromagnetic energy to the reactant gas(es) is likely to change with time of operation of the apparatus, even though the energy source is set to deliver a constant level of power to the decomposition region. Accordingly, the simplistic approach of setting the source of electromagnetic energy to a preselected constant value in order to sense and control the intensity of electromagnetic energy delivered to the decomposition region of a glow discharge deposition system, is not sufficiently accurate to provide a reproducibly controllable level of power.

It is to fill this need for accurately monitoring and reproducibly controlling the intensity of electromagnetic energy in the decomposition region actually decomposing the reactant gas(es) flowing therethrough that the apparatus and method of the instant invention was developed. More precisely, the method and apparatus of the instant invention directly senses the intensity of electromagnetic energy in the decompositon region of glow discharge deposition apparatus by detecting the emission of radiant energy from the excited reactant gas(es) in that decomposition region. A signal indicative of the intensity of the electromagnetic energy actually emitted by the reactant gas(es) is then generated. That signal is utilized in a closed, automatic control loop to assure that the electromagnetic energy acting to decompose the reaction gas(es) remains at a preselected value despite variations in other operating parameters.

The many objects and advantages of the present invention will become clear from the drawings, the detailed description of the invention and the claims which follow.

BRIEF SUMMARY OF THE INVENTION

There is disclosed herein a closed feedback control loop for controlling the intensity of energy developed in the decomposition region of a deposition chamber. More particularly, there is disclosed herein glow discharge apparatus in which a layer of semiconductor material is deposited upon a substrate. The deposition apparatus includes at least one deposition chamber into which a reaction material is introduced and in which decomposition means, including an emitter coupled to a source of electromagnetic energy, it positioned for decomposing the reaction material to deposit said layer of semiconductor material onto the substrate. The improvement of the present invention comprises means for sensing the level of energy in the decomposition region; means for generating a signal indicative of said energy level; and means adapted to respond to the generated signal for controlling the level of energy provided to the decomposition region by said source of energy, whereby the actual intensity of energy provided to decompose the reaction material in the decomposition region can be accurately sensed and reproducibly controlled.

In the preferred embodiment, the energy sensing means is a photodetector operatively disposed proximate the decomposition region for (1) monitoring the energy in the decomposition region, and (2) providing an output signal indicative of the actual level of energy in the decomposition region. Additional means are present for providing a preselected reference signal corresponding to a preselected level of electromagnetic energy; and the signal generating means is adapted to compare the output signal provided by the photodetector to the reference signal. The reference signal providing means may be an adjustable, constant voltage power source and the signal comparing means will include a voltage comparator. The power supply is adapted to respond to a correction signal from the voltage comparator by correspondingly changing the intensity of electromagnetic energy delivered to the decomposition region.

There is also disclosed in the present application a method of sensing the actual intensity of energy within a decomposition region of glow discharge deposition apparatus and controlling the intensity of that energy. The energy is preferably provided by a power supply adapted to decompose the reaction material introduced into the deposition apparatus. The method comprises the steps of operatively disposing an energy sensing means proximate the decomposition region, said energy sensing means adapted to monitor the level of energy in the decomposition region, and provide an output signal indicative of the actual level of energy; providing a preselected reference signal corresponding to a preselected level of energy; comparing the signal provided by the signal sensing means to the preselected reference signal; and generating a correction signal indicative of the actual level of electromagnetic energy sensed in the decomposition region relative to the preselected level of energy, whereby the actual intensity of the energy in the decomposition region can be accurately sensed. The method may also include the additional step of correcting the level of energy provided by the power supply to the decomposition region, whereby the intensity of energy delivered to the decomposition region can also be accurately and reproducibly controlled.

DETAILED DESCRIPTION OF THE DRAWINGS

I. The Photovoltaic Cell

Figure 1:
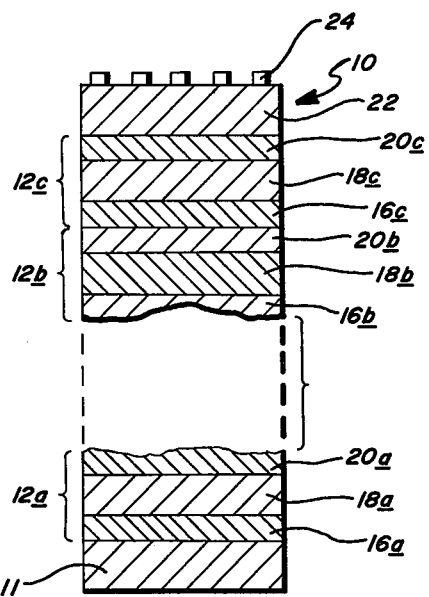
FIG. 1 is a fragmentary, cross-sectional view of a tandem photovoltaic device comprising a plurality of p-i-n type cells, each layer of the cells formed from a semiconductor alloy.

Referring now to the drawings and particularly to FIG. 1, a photovoltaic cell, formed of a plurality of successive p-i-n layers, each of which includes, in the preferred embodiment, a semiconductor alloy, is shown generally by the number 10. It is for the production of this type of photovaltaic device, wherein homogeneous semiconductor layers are successively deposited onto a substrate in either (1) a single chamber batch process, or (2) successive isolated deposition chambers in a continuous process, that the method and apparatus of the present invention for monitoring and controlling the intensity of electromagnetic energy in the decomposition region of a deposition apparatus was developed.

More particularly, FIG. 1 shows a p-i-n type photovoltaic device such as a solar cell made up of individual p-i-n type cells 12a, 12b and 12c. Below the lowermost cell 12a is a substrate 11 which may be transparent or formed from a metallic material such as stainless steel, aluminum, tantalum, molybdenum or chromium, or an insulating material such as glass with or without metallic particles embedded therein. Although certain applications may require a thin oxide layer and/or a series of base contacts prior to deposition of the semiconductor material, for purposes of this application, the term, "substrate" shall include not only a flexible film, but also any elements added thereto by preliminary processing.

Each of the cells 12a, 12b and 12c are fabricated with an amorphous semiconductor body containing at least a silicon or germanium alloy. Each of the semiconductor bodies includes an n-type conductivity layer 20a, 20b and 20c; an intrinsic layer 18a, 18b and 18c; and a p-type conductivity layer 16a, 16b and 16c. As illustrated, cell 12d is an intermediate cell and, as indicated in FIG. 1, additional intermediate cells may be stacked atop the illustrated cells without departing from the spirit or scope of the present invention. Also, although p-i-n cells are illustrated, the intensity monitoring and controlling apparatus and corresponding method of this invention may also be used in (1) deposition apparatus adapted to produce single or multiple n-i-p cells, or (2) in other applications wherein the control of the intensity of energy supplied to a chamber would prove beneficial. Such other applications include, without limitation, plasma etching, plasma polymerization or sputtering operations.

It is to be understood that following the deposition of the semiconductor layers, a further deposition process may be either performed in a separate environment or as a part of a continuous process. In this step, a TCO (transparent conductive oxide) layer 22 is added. An electrode grid 24 may be applied to the device where the cell is of a sufficiently large area, or if the conductivity of the TCO layer 22 is insufficient. The grid 24 shortens the carrier path through the TCO and thus increases the conduction efficiency.

II. The Multiple Glow Discharge Deposition Chambers

Figure 2:
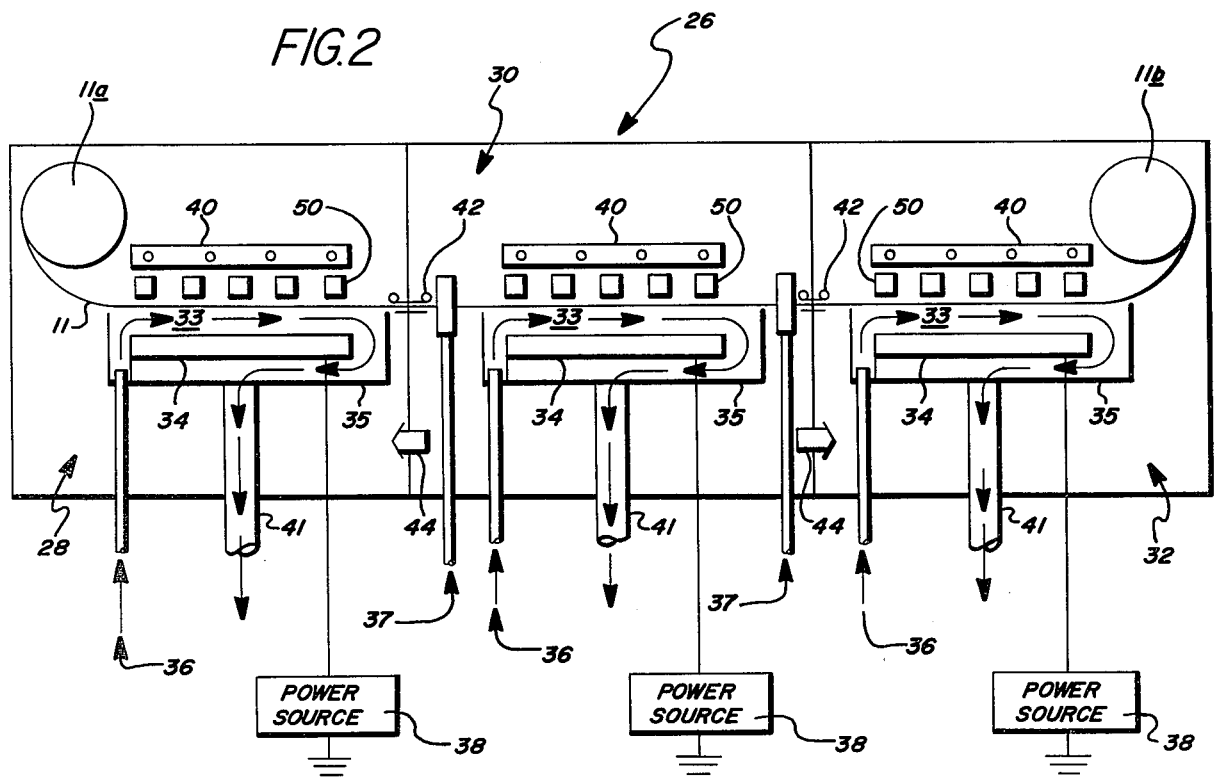
FIG. 2 is a diagrammatic representation of a multichamber glow discharge deposition system adapted for use in the continuous production of photovoltaic devices such as the cells shown in FIG. 1.

Turning now to FIG. 2, a diagrammatic representation of multiple glow discharge chamber deposition apparatus for the continuous production of photovoltaic cells is generally illustrated by the reference numeral 26. The apparatus 26 includes a plurality of isolated, dedicated deposition chambers, each chamber of which is interconnected by a gas gate through which sweep gases and a web of substrate material are adapted to pass.

The apparatus 26 is adapted to mass produce, in the preferred embodiment, large area, amorphous photovoltaic cells having p-i-n type layers deposited on the surface of a web of substrate material 11 which is continually fed therethrough. To deposit the amorphous semiconductor layers required for producing multiple p-i-n type cells, the apparatus 26 includes at least one triad of deposition chambers. Each triad of deposition chambers comprises: a first deposition chamber 28 in which a p-type conductivity semiconductor layer is deposited onto the deposition surface of the substrate 11 as the substrate 11 passes therethrough; a second deposition chamber 30 in which an intrinsic amorphous semiconductor layer is deposited atop the p-type alloy layer on the deposition surface of the substrate 11 as the substrate 11 passes therethrough; and a third deposition chamber 32 in which an n-type conductivity semiconductor layer is deposited atop the intrinsic layer on the deposition surface of the substrate 11 as the substrate 11 passes therethrough. It should be apparent that, (1) although, only one triad of deposition chambers has been illustrated, additional triads or additional individual chambers may be added to the apparatus to provide the machine with the capability of producing photovoltaic cells having any number of p-i-n type semiconductor layers; (2) the electromagnetic energy monitoring and control system of the present invention is applicable to any type of deposition apparatus, whether continuous or batch process, whether energized by microwave, radio frequency, alternating current, direct current, etc. and whether dealing with semiconductors, optical coatings, refractory materials, etc.; and (3) the substrate supply core 11a and the substrate take-up core 11b are shown in the deposition chambers for illustrative purposes only, while in reality the cores would be housed in separate chambers operatively connected to the deposition chambers and sealed from environmental conditions.

Each deposition chamber 28, 30 and 32 of the triad is adapted to deposit a single semiconductor material, by glow discharge deposition onto the substrate 11. To that end, each of the deposition chambers 28, 30 and 32 includes: a cathode 34; a shield 35 disposed about each of the cathodes 34; a process gas supply conduit 36 for introducing reactant gas mixtures into the chambers adjacent the cathodes; a power source 38 such as an alternating current generator; an evacuation conduit 41 for removing unused, nondeposited and/or spent process gases; a plurality of transversely extending, warpage preventing magnetic elements 50; a plurality of radiant heating elements shown schematically as 40; and a gas gate 42 operatively connecting the intrinsic deposition chamber 30 to each of the dopant chambers 28 and 32. Further, an inert sweep gas conduit 37 is disposed, proximate the gas gates 42, an opposed sides of the intrinsic deposition chamber 30.

The supply conduits 36 are operatively associated with the respective cathodes 34 to deliver process gas mixtures to a decomposition region 33 created in each deposition chamber between said cathodes 34 and the grounded substrate 11. The cathode shields 35 are adapted to operate in conjunction with the web of substrate material 11 and the evacuation conduit 41 to substantially confine the flow of reaction gas(es) through the decomposition region 33 to a preselected path of travel and to likewise confine the plasma within said decomposition region 33 of the respective deposition chambers.

The power sources 38 operate in conjunction with the cathodes 34, the radiant heaters 40 and the grounded substrate 11 to form an ionized plasma from the reaction gas(es) entering the decomposition region, thereby disassociating and recombining those process gases into deposition species. The deposition species are then deposited onto the bottom surface of the substrate 11 as layers of semiconductor material. The substrate 11 is maintained substantially flat by the plurality of rows of magnetic elements 50 which provide an attractive force urging the substrate upward, out of its normal sagging path of travel.

To form the photovoltaic cell 10 illustrated in FIG. 1, a p-type semiconductor layer is deposited onto the substrate 11 in the deposition chamber 28, an intrinsic amorphous semiconductor layer is deposited atop the p-type layer in the deposition chamber 30 and an n-type semiconductor layer is deposited atop the intrinsic layer in the deposition chamber 32. As a result, the apparatus 26, deposits at least three semiconductor layers onto the substrate 11, the intrinsic layer deposited in deposition chamber 30 differing in composition from the layers deposited in deposition chambers 28 and 32 by the absence of at least one element which will be referred to as the dopant or doping species.

It is important that the various layers making up the photovoltaic device 10, illustrated in FIG. 1 be of precisely controlled compositions and thicknesses in order to produce a high efficiency photovoltaic device. It is therefore necessary to be able to accurately control the intensity of electromagnetic energy delivered by the source 38 to set up an electromagnetic field in the decomposition region 33 of the chambers of the deposition apparatus 26. The following section will describe the apparatus which provides such a control mechanism.

III. Measuring and Controlling the Energy In The Decomposition Region

Figure 3:
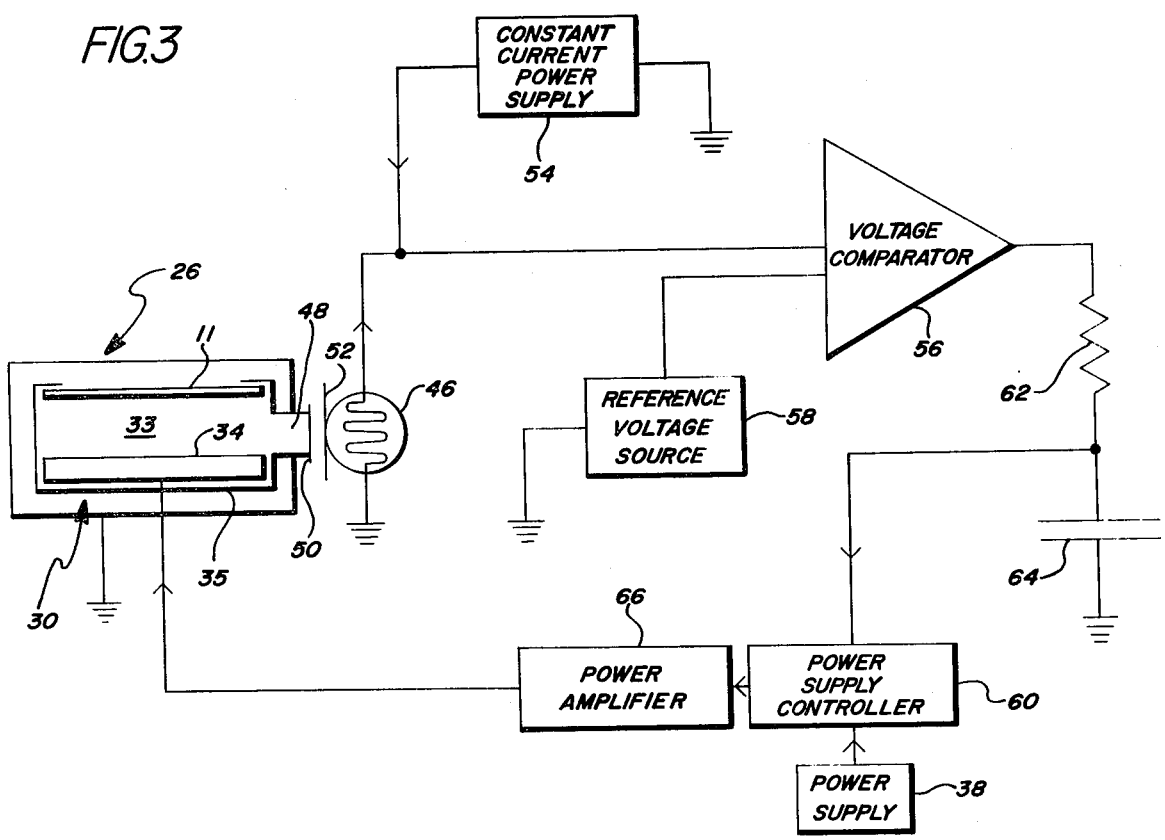
FIG. 3 is a schematic representation of one embodiment of the energy measuring and controlling apparatus of the present invention, said apparatus operatively disposed relative to the decomposition region of a deposition chamber.

FIG. 3 is a schematic representation of one preferred embodiment of the apparatus of the present invention showing the operative disposition of the major components utilized to sense and control the intensity of electromagnetic energy in the decomposition region 33 of the glow discharge deposition apparatus 26 for decomposing the reaction gases introduced thereinto.

The deposition apparatus 26 of FIG. 2, although of reduced size, is intended to generally correspond to the apparatus depicted by reference numeral 26 in FIG. 2; however, for the sake of brevity and clarity only one chamber 30 thereof is illustrated. As previously described and as clearly shown in FIG. 3, the apparatus 26 includes a vacuum chamber 30 having a cathode plate 34, a grounded substrate 11, and a cathode shield 35 therein, all cooperating to define the decomposition region 33. It is in this decomposition region 33 that reaction gases are subjected to the effects of an electromagnetic field. The field is developed when the source of electromagnetic energy 38 energizes the cathode plate 34 to which it is operatively coupled.

In operation, the cathode 34 delivers electromagnetic energy to the reactant gas(es) flowing through the decomposition region 33 of the deposition chamber, thereby exciting the atoms of those gas(es). The atoms of gas(es) thus excited emit radiant energy which is, typically, visible to the human eye. It is to be noted that, while the foregoing emission of visible radiant energy has been termed "glow discharge", the radiant energy emitted by the excited atoms of reactant gas(es) need not be visible for such a process to be so termed.

As depicted in FIG. 3, a photodetector 46 is operatively disposed so as to receive the radiation emitted from the excited reactant gas(es) in the decomposition region 33 of the deposition chamber 30. More specifically, the photodetector 46 is disposed exteriorly of the vacuum chamber 30 in a sealed photodetector adapter assembly 48. The photodetector assembly 48 includes a transparent window 50 through which the visible radiant energy passes from the deposition region 33 of the chamber 30 for sensing by the photodetector 46. A filter 52 may be disposed in the optical path of the radiation to appropriately adjust the intensity etc. of the incoming energy. Further, through proper selection of the filter 52, spurious radiant energy, such as that emitted by substrate heaters, may be eliminated, thereby increasing the sensitivity of the monitoring system. While the photodetector 46 is depicted in FIG. 3 as being operatively disposed exteriorly of the vacuum chamber 30, it may also be placed either (1) directly within the chamber, or (2) remotely located and communicating with the decomposition regions by means of fiber optics or the like. All such embodiments are within the spirit and scope of the present invention.

In the preferred embodiment, the photodetector 46 is a photoconductive cell, the electrical resistance thereof changing in response to changes in the intensity of illumination incident thereupon. One such acceptable photodetector is the model VT542L cadmium selenide cell distributed by Newark Electronics. Other types of photoconductive cells such as cadmium sulfide cells may also be employed. And, in other preferred embodiments of the instant invention, other types of photodetectors such as photodiodes and bolometers may be advantageously employed. The choice of the type of photodetector 46 is dependent upon, inter alia, the radiant energy emitted from the decomposition region 33 of the deposition chamber 30 of the deposition apparatus 26; that is to say, the detector must be appropriately sensitive to the particular wavelengths of light emitted.

A constant current power supply 54 is operatively connected to the photodetector 46 for providing a constant current thereto. Since the resistance of the photodetector 46 changes in response to light it receives and senses, by applying a constant current to the photodetector 46, the voltage drop thereacross is directly correlatable to the intensity of illumination from the emitted energy sensed by the photodetector 46. Operatively connected to the photoconductor 46 is a preselected voltage comparator 56 which is adapted to receive a reference voltage signal from a reference voltage source 58 operatively associated therewith.

It is the function of the voltage comparator 56 to (1) compare the voltage across the photodetector 46 with the reference voltage provided by the reference voltage source 58, and (2) generate a correction signal indicative of the level of energy in the decomposition region relative to the preselected level of energy. The correction signal is communicated to a power supply controller 60 which is operatively connected and adapted to control the energy output forwarded from the power supply 38, and amplified by a power amplifier 66, to the emitter (such as the cathode plate 34) disposed within the deposition chamber 30. One acceptable model of voltage comparator 56, for use in an open loop mode, is the Model 741 operational amplifier manufactured by Signetics Corporation, although other similar operational amplifiers may also be employed.

Also included in the embodiment illustrated in FIG. 3 is a low pass filter formed by a resistor 62 and a capacitor 64, both of which are operatively associated with the output correction signal generated by the voltage comparator 56. The resistor 62, in the preferred embodiment having a value of approximately 10 K ohms, and the capacitor, in the preferred embodiment having a value of approximately 100 microfarads, cooperate to form said low pass filter for eliminating unnecessary high frequency signals from said output correction signal. The power supply controller 60 includes any well known type of a modulating system, which is adapted to change the intensity of the electromagnetic power generated by the power supply 38 in response to the output correction signal received from the voltage comparator 56. The RCA model SK3050 dual gate transistor is particularly well suited for such a task, with the first gate thereof receiving the correction signal from the voltage comparator 56 and the other gate operatively connected to the power supply 38.

The apparatus for accurately sensing and reproducibly controlling the level of electromagnetic energy delivered to the decomposition region 33 of the deposition chamber 30 disclosed in FIG. 3 operates in the following manner. Upon energization, the constant current power supply 54 delivers a constant, preselected current to the photodetector 46. The photodetector 46 is illuminated to a level dependent upon the intensity of the glow emitted by the atoms of the reactant gas(es) in the decompostion region 33 of the deposition chamber 30 which have been energized by the electromagnetic field established by the delivery of electromagnetic energy to the cathode 34. Since the photoemission from these excited reaction gas(es) is a monotonically increasing function of the electromagnetic energy supplied by the power source 38, the voltage across the photodetector 46 may be correlated to the actual intensity of the electromagnetic field established in the decomposition region 33 of the deposition chamber.

The voltage across the photodetector 46 is compared by the voltage comparator 56 to the preselected reference voltage provided by the reference voltage source 58. The comparator 56 then generates an output correction signal indicating the relative levels of the two voltages. The voltage comparator 56, described hereinabove, has a bistable output, i.e., the output signal may either be of high or low magnitude depending upon the intensity of the signal from the photodetector 46 relative to the preselected signal from the reference source 58. If the voltage signal from the photodetector 56 is greater than the voltage signal provided by the reference source 58, the voltage comparator 56 emits a high magnitude correction signal; conversely, if the voltage signal from the photodetector 46 is lower than the voltage signal from the reference voltage source 58, the voltage comparator 56 emits a low magnitude correction signal. Finally, the voltage comparator 56 is adapted to emit a oscillating signal if the two voltage signals are approximately equal.

It is for this reason that the low pass filter is important. The low pass filter functions to integrate the output correction signal from the voltage comparator 56 over a period of time, and thereby smooth out variations in the correction signal, thus eliminating unnecessary cycling of the power supply controller 60. More particularly, rapid oscillations in the output correction signal generated when the two voltage signals are nearly equal will be averaged out over time and thus cancelled, while the larger voltage signals, indicative of noteworthy voltage deviations, will be forwarded to pass to the power supply controller 60.

The power supply controller 60 is an integral link in the automatic feed back loop, said loop adapted to adjust the amount of electromagnetic energy delivered by the power supply 38 to the cathode 34, and thus, ultimately control the intensity of the electromagnetic field to which the reactant gas(es) are subjected as the gas(es) flow through the decomposition region 33 of the deposition chamber 30.

It should thus be obvious that the components depicted in FIG. 3 and described hereinabove form a closed loop control system for setting and maintaining the electromagnetic energy delivered to the decomposition region 33 at a predetermined level. This is expeditiously and accurately accomplished by adjusting the reference signal from voltage source 58.

Figure 4:
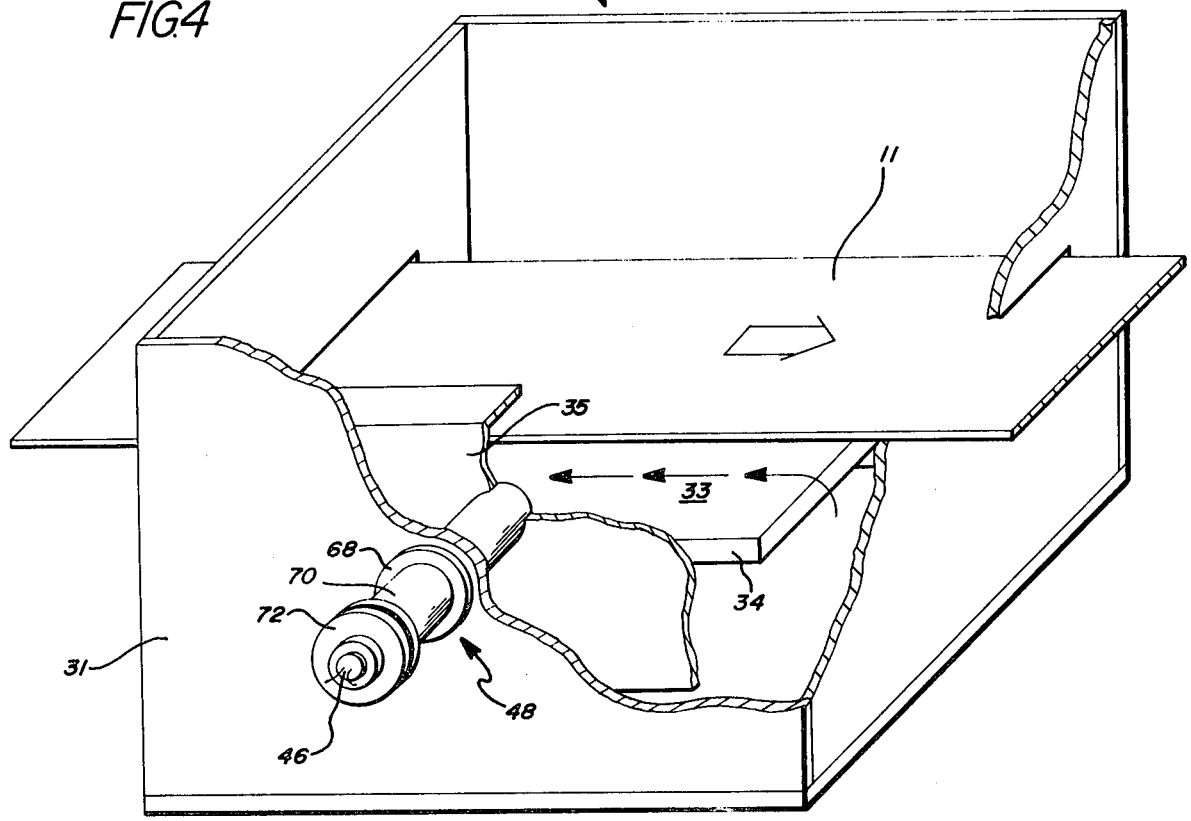
FIG. 4 is an enlarged, partially cut-away, perspective view of one deposition chamber of a multi-chamber glow discharge deposition system illustrating the operative disposition of a photodetector to measure the intensity of electromagnetic energy delivered to the decomposition region of that chamber.

Turning now to FIG. 4, the mechanism by which the photodetector 46 is operatively disposed within a symbolic one of the vacuum chambers, for example 30, of the deposition apparatus 26 is shown. The photodetector 46 is housed within a photodetector mounting assembly 48 and is operatively disposed to detect the intensity of the electromagnetic field developed within the decomposition region 33. The photodetector mounting assembly 48 is a generally elongated, tubular member which, when operatively disposed, passes through (1) the exterior wall 31 of the vacuum chamber 30 and (2) the cathode shield 35 which sealingly surrounds the decomposition region 33. An air-tight seal 68 including a transparent window, provides a seal capable of withstanding vacuum pressures of less than $10^{-7}$ torr and prevents ambient conditions from penetrating the deposition chamber 30. The transparent window is operatively disposed to allow radiant energy from the decomposition region 33 to pass to the photodetector 46 for the detection thereof. The seal 68 can be formed by an O-ring and the transparent window can be formed from a transparent material such as glass or quartz. Mechanically connected to the seal 68 is a cylindrically-shaped, hollow sleeve 70 to which a fixture 72 having the photodetector 46 mounted therein is coupled. It is the function of the sleeve 70 and the fixture 72 to operatively retain the photodetector 46 in position to receive radiant energy emanating from the decomposition region 33, while shielding the photodetector 46 from ambient illumination. The sleeve 70, fixture 72 and mounting assembly 48 are, consequently, preferably made of opaque metallic materials.

It should be obvious that many variations of the embodiments described hereinabove may be made in keeping with the spirit of the instant invention. For example, the electromagnetic energy detecting apparatus depicted in FIG. 3 could be operated as part of an open loop control system. That is, the output correction signal from the voltage comparator 56 could be utilized in conjunction with a readable display to directly indicate to the operator of the apparatus the level of electromagnetic energy emanating from decomposition region 33. The operator could then utilize that information to manually adjust the power supply 38 to the preselected level of electromagnetic energy.

It may also be desirable to utilize an alternative type of photodetector 46 such as a photovoltaic cell. Of course the use of a photovoltaic cell would require modification of the associated circuitry to measure the photocurrent output rather than the voltage. For example, (1) a constant current power supply could be substituted for the reference voltage source 58, and (2) circuitry for comparing the photocurrent from the photovoltaic cell with the reference current could be utilized in a manner analogous to the method shown in the FIG. 3 embodiment.

The structual disposition of the photodetector 46 of FIG. 4 could be varied in a variety of ways without departing from the spirit of the present invention. It is possible to place the detector 46 within the vacuum chamber 30 itself. Fiber optics could be utilized to convey the signal, which is indicative of the intensity of electromagnetic energy in the decomposition region 33, to the photodetector 46.

It should be understood that the present invention is not limited to the precise structure of the illustrated embodiments. It is intended that the foregoing description of the presently preferred methods be regarded as illustrative rather than as limiting. It is the claims which follow, including all equivalents, which are intended to define the scope of this invention.

What we claim is:

1. In a plasma glow discharge deposition apparatus which is adapted to deposit a layer of semiconductor material upon a substrate, said apparatus including: at least one vacuum chamber; reaction gases adapted for introduction into said chamber; an electrode operatively disposed within said chamber in spaced relation to said substrate; a power supply coupled to said electrode for providing electromagnetic energy to the electrode so as to (1) form a plasma for decomposing the reaction gases in a decomposition region which is formed between the electrode and the substrate, and (2) deposit the layer of semiconductor material onto the substrate; the improvement comprising in combination:

a photosensor operatively disposed to (1) receive illumination emanating from the plasma and (2) generate an output signal correlatable with the intensity of the illumination;

a reference signal source independent of the photosensor, said source adapted to provide a preselected reference signal, whereby said reference signal is independent of the intensity of illumination from the plasma;

comparator means adapted to compare the output signal of the photosensor with the reference signal and generate a control signal indicative of the difference between said output and reference signals, and power supply control means adapted to (1) receive the control signal and (2) adjust the intensity of power delivered by the power supply in response to the control signal, whereby the electromagnetic energy actually delivered to the plasma from the electrode may be maintained at a preselected level.

2. Apparatus as in claim 1, wherein the photosensor is a photoconductive device which changes its electrical resistivity in response to the level of illumination incident thereupon; the reference signal source is adapted to provide a preselected reference voltage; the comparator means is a voltage comparator; and said apparatus further includes:

a constant current power supply operatively disposed to provide a preselected, constant flow of electrical current through the photoconductive device, whereby a given intensity of illumination from the plasma incident upon the photoconductive device provides a corresponding voltage across the photoconductive device.

3. Apparatus as in claim 1, wherein the substrate is a generally elongated web and said apparatus further includes:

means for continuously advancing the elongated web through the vacuum chamber for the deposition of the semiconductor material thereupon.

* * * * *